(12) United States Patent  
Omata (10) Patent No.: US 7,583,383 B2  
(45) Date of Patent: Sep. 1, 2009

(54) BIOLOGICAL PROPERTY CHECK DEVICE USING LIGHT

(75) Inventor: Sadao Omata, Chiyoda-ku (JP)

(73) Assignee: Nihon University, Tokyo (JP)

( * ) Notice: Subject to any disclaimer, the term of this patent is extended or adjusted under 35 U.S.C. 154(b) by 483 days.

(21) Appl. No.: 10/572,062

(22) PCT Filed: Sep. 30, 2004

(86) PCT No.: PCT/JP2004/014338

§ 371 (c)(1),
(2), (4) Date: Mar. 15, 2006

(87) PCT Pub. No.: WO2005/030058

PCT Pub. Date: Apr. 7, 2005

(65) Prior Publication Data

US 2008/0037021 A1    Feb. 14, 2008

(30) Foreign Application Priority Data

Sep. 30, 2003    (JP)  ............................. 2003-341880

(51) Int. Cl.
G01N 21/55    (2006.01)
(52) U.S. Cl. .................................... 356/445
(58) Field of Classification Search ................ 356/445, 356/495, 5.1, 5.01; 600/310
See application file for complete search history.

(56) References Cited

U.S. PATENT DOCUMENTS 5,360,004 A * 11/1994 Purdy et al. ................. 600/310
5,460,177 A * 10/1995 Purdy et al. ................. 600/436
5,725,480 A * 3/1998 Oosta et al. ................. 600/310
5,766,137 A    6/1998 Omata
5,792,051 A * 8/1998 Chance ........................ 600/310
7,007,554 B2 * 3/2006 Omata ........................... 73/800
7,065,392 B2 * 6/2006 Kato ............................ 600/323
2004/0142402 A1    7/2004 Maruo et al.

FOREIGN PATENT DOCUMENTS

| JP | A 62-164434 | 7/1987 |
| JP | A 07-049306 | 2/1995 |
| JP | A 09-145691 | 6/1997 |
| JP | A 2003-144421 | 5/2003 |

* cited by examiner

*Primary Examiner*—Tarifur R. Chowdhury
*Assistant Examiner*—Isiaka O Akanbi
(74) *Attorney, Agent, or Firm*—Oliff & Berridge, PLC (57) ABSTRACT

A biological property check device includes a plurality of probes (20) each having a light emitting element (26) for applying light to a biological tissue and a light reception element (28) for detecting the reflected light. Each probe (20) is successively selected by a switch circuit (60) under control of a control section (76) and connected to a property calculation section (64). The property calculation section (64) includes a phase shift circuit for changing the frequency according to the phase difference between the input waveform to the light emitting element (26) and the output waveform from the light reception element (28). According to the frequency change, the property of the biological tissue is calculated. The property calculated is displayed on a display section (74) via a data collection section (70) and a display processing section (72).

5 Claims, 8 Drawing Sheets

BIOLOGICAL PROPERTY CHECK DEVICE USING LIGHT

TECHNICAL FIELD

The present invention relates to a detection apparatus for optically evaluating a property of a biological material, and more particularly to a material property detection apparatus including a light emitting element for applying light to a living body and a light receiving element for receiving light from the living body.

BACKGROUND ART

Transmission examinations and tomographic examinations by means of X-ray radiography, for example, X-ray CT examinations are often performed for examining changes in dermal tissues and internal organs in a living body. To avoid problems associated with X-ray exposure, methods for optical examination using laser beams or the like have been proposed as alternatives. For example, Japanese Patent Laid-Open Publication No. 2003-144421 discloses a method in which a light emitter/receiver probe is placed against a skin surface of a living body so as enable application of a near-infrared light, and the spectrum of the received light is measured so as to determine a concentration of a component in the body skin tissue based on an analytical formula. Further, Japanese Patent Laid-Open Publication No. Hei 7-49306 discloses irradiating light on a living body using a multi-mode oscillating laser as the light source, synthesizing reflected light received from sites having different refractive indices within the living body, and performing spectroscopic analysis of the synthesized light for each oscillating mode so as to obtain light wave echo tomographic images.

As described above, in conventional techniques for optically determining a biological material property, differences in spectral distributions between the incident light and the reflected light are employed. Accordingly, it is necessary to use a large-scale system including many devices such as a light source having stable wavelength, a spectroscopic device for analyzing spectrums, and an analyzer for analyzing the spectral changes between the incident light and the reflected light.

For example, when performing an examination of a tumor on a body surface or a lump located within a living body, even when only a very limited region needs to be examined, a large-scale apparatus must be used, resulting in inconvenience and high costs.

An advantage of the present invention is to offer a solution to the above-noted problem of the conventional techniques by providing a simply-configured detection apparatus for optically determining a property of a biological material. The present invention advantageously provides a detection apparatus for optically determining a biological material property which measurement of a two-dimensional distribution of a material property using an apparatus of simple configuration.

DISCLOSURE OF THE INVENTION

Figure 1:
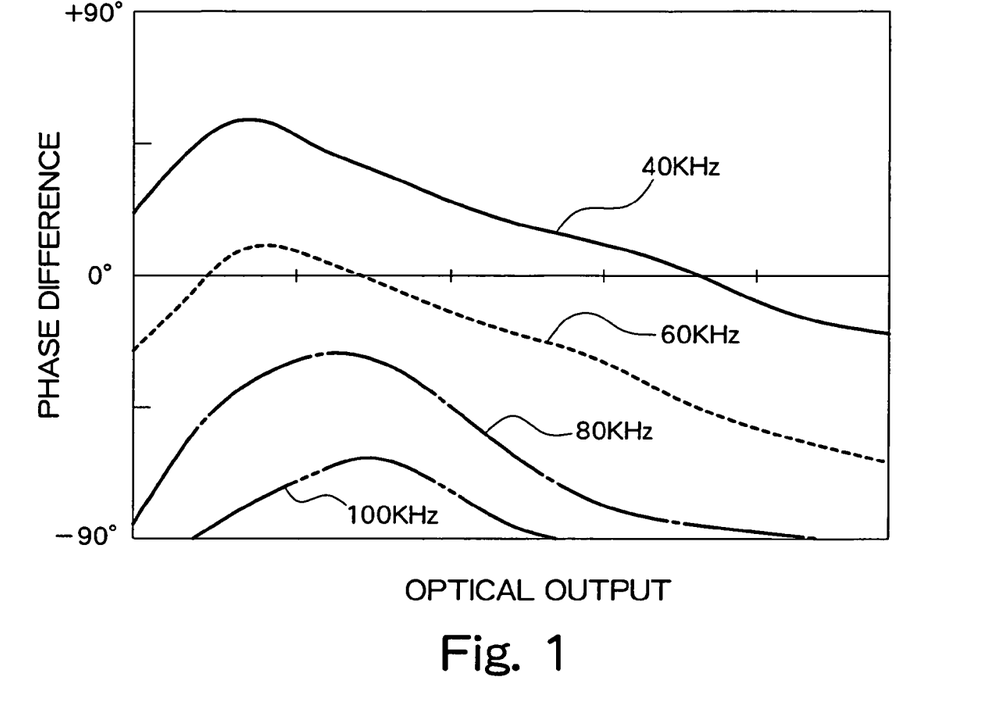
FIG. 1 is a diagram explaining the observation results which serve as the basis for the concept of the present invention, and shows that, when periodic light is applied from a light emitting element to a body tissue and the reflected light is detected by means of a light receiving element, a phase difference is observed between the input signal into the light emitting element and the output signal from the light receiving element.

The present invention is based on the discovery that, when a periodic optical output is applied to a living body by driving a light emitting element, and changes in the reflected light are then observed by capturing the changes using a light receiving element, generation of a phase difference between the periodic input signal which drives the light emitting element and the periodic output signal extracted from the light receiving element can be confirmed. FIG. 1 shows example observation results obtained by applying periodic light emitted from an LED (light emission diode) to fat tissue (which is one type of biological tissue), detecting the reflected light by means of a photodiode, and observing the phase difference between the input signal supplied to the LED and the output signal from the photodiode. In FIG. 1, optical output from the LED is given on the horizontal axis, while phase difference between the input signal and the output signal is given on the vertical axis. The varied parameter in FIG. 1 is the frequency of the input signal. As shown in FIG. 1, when monitoring the output signals from the photodiode obtained by applying periodic lights to a biological tissue, phase differences which depend on the optical output and the input frequency are detected. Further, it has also been confirmed that the magnitude of phase difference is varied by different biological tissues. Accordingly, it can be understood that the phase difference denotes a biological material property with respect to light.

The present inventor previously devised a phase shift method, which is a method for accurately determining a phase difference between an input signal and an output signal (refer to Japanese Patent Laid-Open Publication No. Hei 9-145691). In the present invention, the phase shift method is applied to the measurement of the phase difference generated between the input signal and the output signal when light is introduced into a living body, so as to accurately and quantitatively determine a property of a biological material (a biological material property) with respect to light.

In consideration of the above-noted findings, a detection apparatus for optically determining a biological material property according to the present invention comprises a probe base and a probe supported on the probe base. The probe includes a light emitting element for applying light to a living body and a light receiving element for receiving light from the living body. The detection apparatus further comprises an amplifier having an input terminal connected to a signal output terminal of the light receiving element, and a phase compensation circuit provided between an output terminal of the amplifier and a signal input terminal of the light emitting element for changing the signal frequency so as to cause any phase difference between an input waveform into the light emitting element and an output waveform from the light receiving element to become zero. The detection apparatus further comprises a frequency difference detector which measures a frequency of a self-induced oscillation generated when the phase difference is made to become zero by means of a feedback loop formed by the probe, the amplifier, and the phase compensation circuit, and detects a difference between a frequency obtained when receiving light from the living body by applying light from the probe to the living body and a frequency obtained when such light is not applied to the living body. The detection apparatus further comprises output means for outputting the detected frequency difference as a material property of the living body.

According to another aspect, a detection apparatus for optically determining a biological material property according to the present invention comprises a probe base and a plurality of probes two-dimensionally arranged and supported on the probe base. Each probe includes a light emitting element for applying light to a living body and a light receiving element for receiving light from the living body. The detection apparatus further comprises a material property calculator provided so as to be connectable between a signal input terminal of the light receiving element and a signal output terminal of the light emitting element in each probe for calculating a material property of the living body, a switch circuit for successively switching connection of the material property calculator to the respective probes, and a display unit for providing a two-dimensional display of the material properties calculated for the respective probes. The material property calculator comprises an amplifier having an input terminal connected to a signal output terminal of the light receiving element, and a phase compensation circuit provided between an output terminal of the amplifier and a signal input terminal of the light emitting element for changing the signal frequency so as to cause any phase difference between an input waveform into the light emitting element and an output waveform from the light receiving element to become zero. The material property calculator further comprises a frequency difference detector which measures a frequency of a self-induced oscillation generated when the phase difference is made to become zero by means of a feedback loop formed by the probe, the amplifier, and the phase compensation circuit, and detects a difference between a frequency obtained when receiving light from the living body by applying light from the probe to the living body and a frequency obtained when such light is not applied to the living body. The detection apparatus determines a material property of the living body based on a two-dimensional distribution of the frequency differences.

The display unit is preferably provided on the probe base on a rear surface located opposite from the surface on which the probes are arranged.

Preferably, the detection apparatus for optically determining a biological material property according to the present invention further comprises a receiving portion provided on a rear surface of the probe base for receiving the display unit, a base-side connector provided at a portion of the receiving portion for connecting with the display unit, and a signal line drawn out from the display unit and including at one end a display-side connector which is detachably connected to the base-side connector. The display unit is preferably mounted on the receiving portion of the probe base while the display-side connector of the signal line remains connected to the base-side connector.

Further, in the detection apparatus for optically determining a biological material property according to the present invention, the probe base preferably includes an external connector for connecting with an external device, and the display-side connector preferably has a structure which is also connectable to the external connector.

As described above, according to the detection apparatus for optically determining a biological material property as provided by the present invention, a phase difference between the input waveform into the light emitting element and the output waveform from the light receiving element is converted into a frequency difference by means of the phase shift method. In comparison to performing quantitative measurement of phase difference, measurement devices having much higher accuracy can be employed in quantitative measurement of frequency. Accordingly, optical detection of a biological material property can be performed in a simple manner which only involves use of components such as electronic circuits and a frequency measurement device in addition to the light emitter and receiver elements.

Further, by two-dimensionally arranging the probes composed of pairs of light emitter and receiver elements, a biological material property with respect to light can be measured and displayed in a two-dimensional manner. By employing an arrangement in which the display unit for providing a two-dimensional display is integrally mounted on the rear surface of the probe base, an operator of the device can observe and be aware of the real-time two-dimensional distribution of the biological material property with respect to light as they perform the examination by, for example, pressing the probe base against a body tissue. Alternatively, by adopting an arrangement in which the display unit is detachable from the probe base and the display unit is connected to the probe base via a signal line, a patient performing self-examination by, for example, pressing the probe base against their own body tissue, can observe and be aware of the real-time two-dimensional distribution of the optical material property in the body by placing the display unit at a location viewable during the self-examination.

BEST MODE FOR CARRYING OUT THE INVENTION

Figure 2:
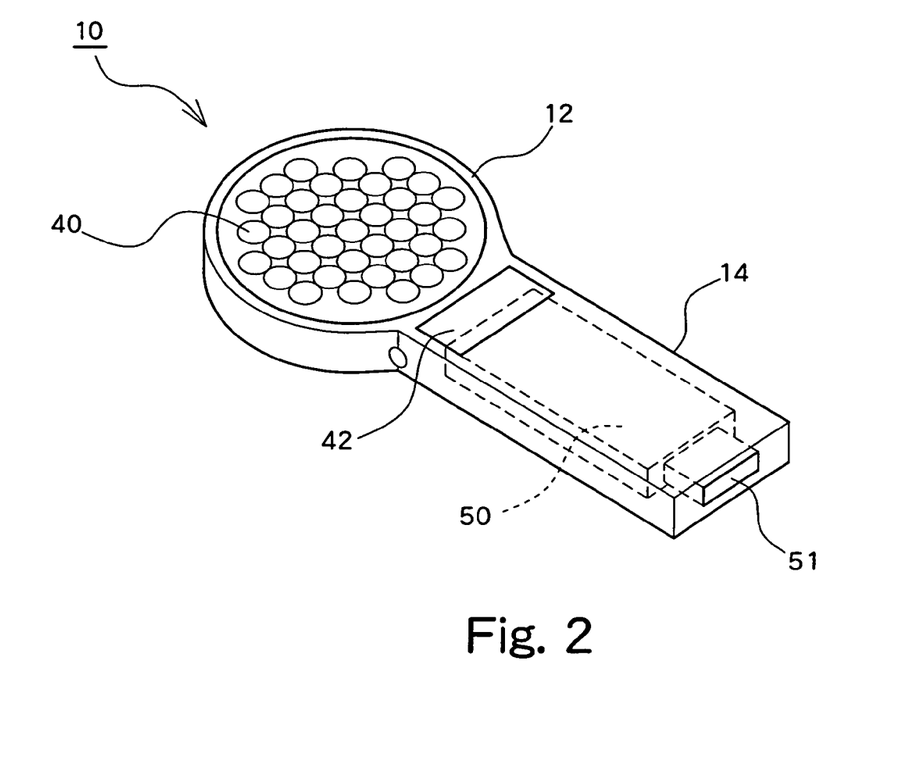
FIG. 2 is a perspective view from the upper side of a material property detection apparatus according to a first embodiment of the present invention.
Figure 3:
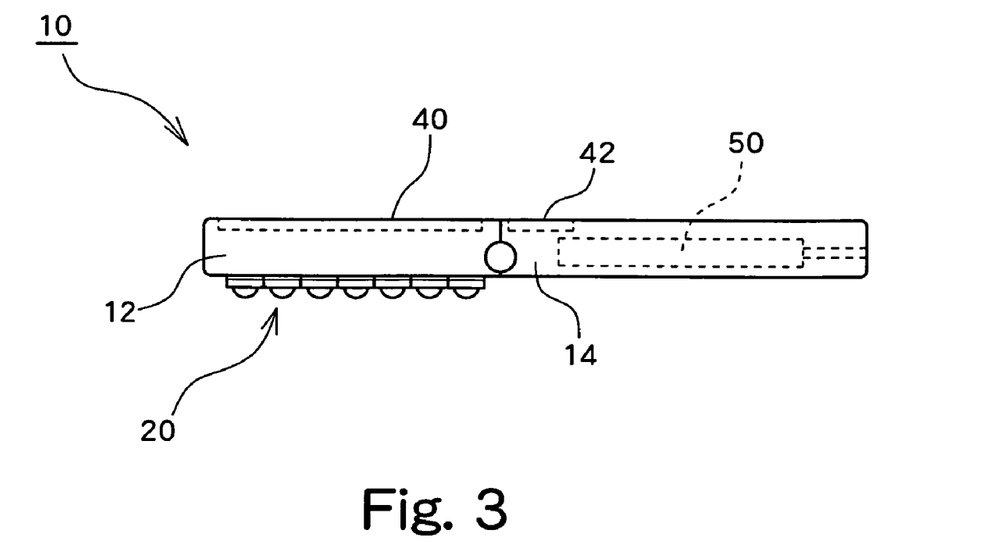
FIG. 3 is a side view of the material property detection apparatus according to the first embodiment of the present invention.
Figure 4:
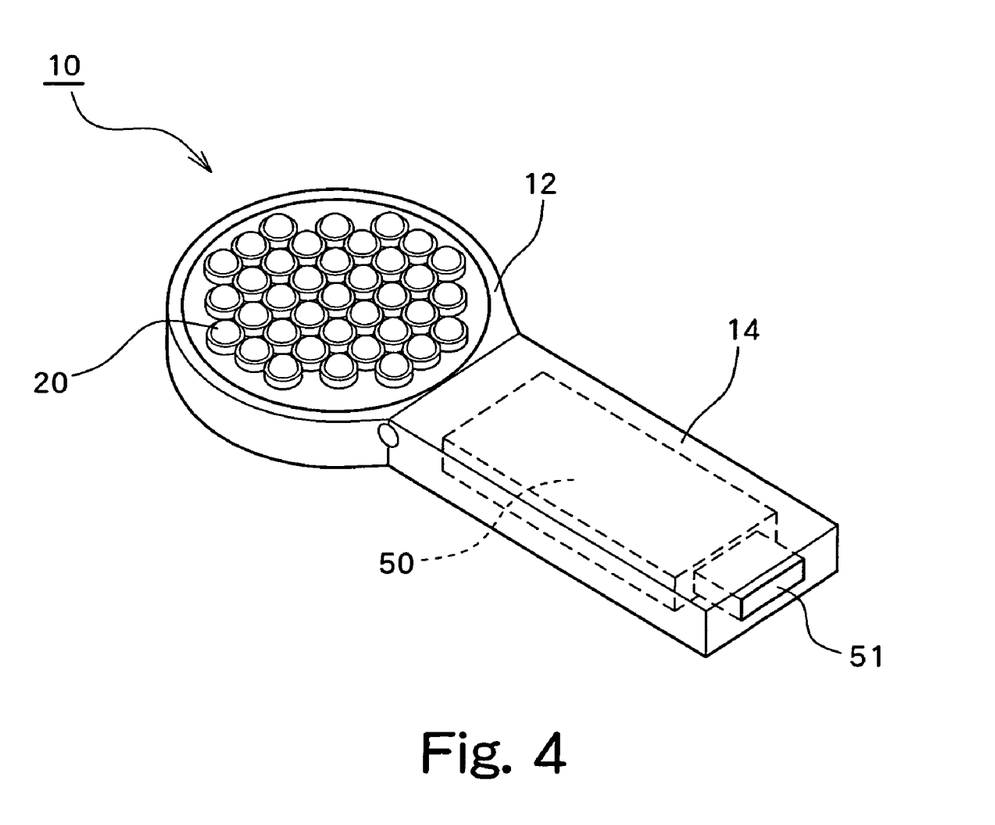
FIG. 4 is a perspective view from the lower side of the material property detection apparatus according to the first embodiment of the present invention.

Embodiments of the present invention are described in detail below referring to the drawings. FIGS. 2-4 are upper perspective view, side view, and lower perspective view, respectively, showing a detection apparatus 10 for optically determining a property of a biological material (hereinafter simply referred to as "material property detection apparatus") according to a first embodiment of the present invention. As shown in these drawings, the material property detection apparatus 10 includes a disk-shaped probe base 12, as well as a grip portion 14 which extends from the probe base 12 and is gripped by hand.

The probe base 12 is a disk-shaped member which supports on its lower surface a plurality of two-dimensionally arranged probes 20 that are to be pressed against a surface of a living body, and which supports on its upper surface a plurality of display elements 40 that are two-dimensionally arranged corresponding to the respective probes 20. For example, the probe base 12 may be formed by two-dimensionally arranging approximately 40 to 50 probes 20 and 40 to 50 display elements 40 on a plastic molded member having a diameter of approximately 60 mm and a thickness of approximately 20 mm. Further, a small-sized display device 42 may be arranged on the upper side.

The grip portion 14 is a handle-shaped member which is fixedly connected to the probe base 12 and has a size appropriate for being stably gripped by hand. For example, the grip portion 14 may be a plastic molded member having a thickness of approximately 20 mm (matching the thickness of the above-described probe base 12), a handle width of approximately 45 mm, and a length of approximately 100 mm.

Located inside the grip portion 14 is an electronic circuit section 50 which calculates a material property of a body tissue contacted by the respective probes 20 based on input and output signals of the probes 20, and performs signal processing for displaying the calculated property as a two-dimensional distribution. An output from the electronic circuit section 50 may be supplied via an external interface 51 to an external diagnostic device or the like (not shown). Alternatively, a part or entire portion of the electronic circuit section 50 may be located outside the grip portion 14, and the electronic circuit section 50 may be connected to the probes 20 and the display elements 40 via a signal line. Details of the electronic circuit section 50 are described further below.

Figure 5:
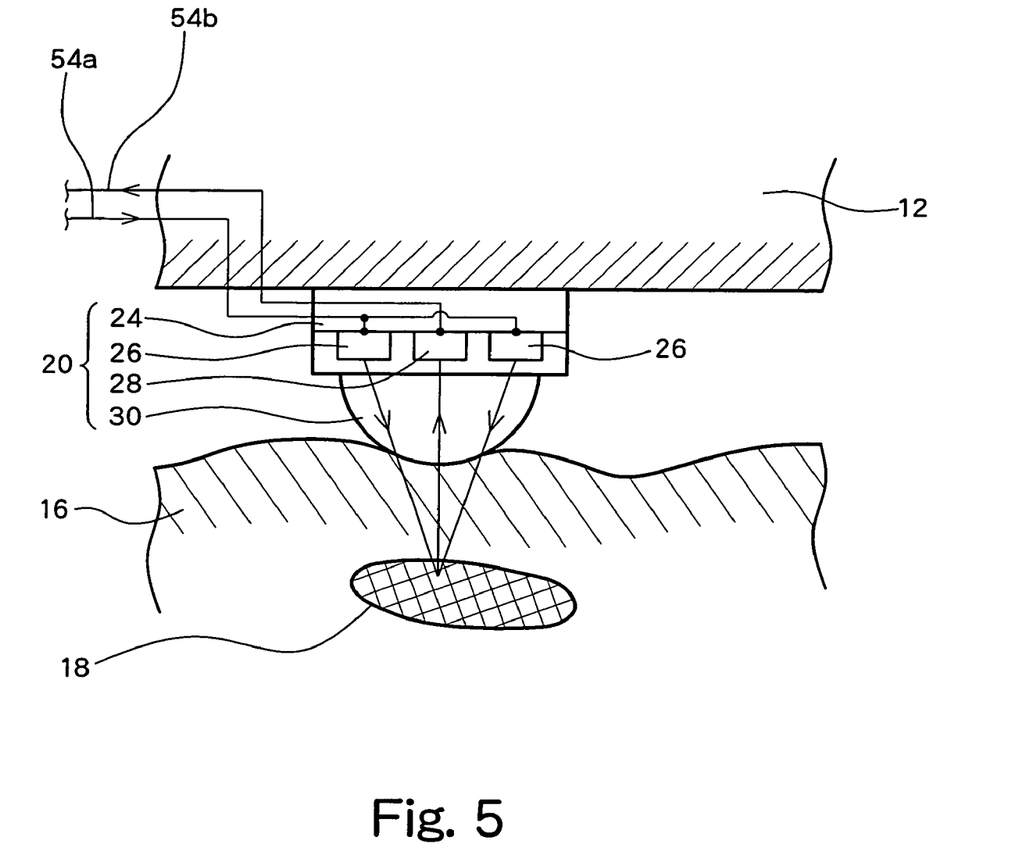
FIG. 5 is a detailed view showing a portion around a probe in the first embodiment of the present invention.

A single probe 20 is configured by arranging a single light emitting element and a single light receiving element adjacent to one another. Alternatively, in order to efficiently receive reflected light, a single probe 20 may be formed by arranging multiple light emitting elements around a single light receiving element. FIG. 5 is a detailed view showing a portion around a single probe 20 which is composed of two light emitting elements 26 and one light receiving element 28. The probe 20 is configured by arranging the light emitting elements 26 and the light receiving element 28 on a mount 24 (on its lower surface in FIG. 5) and covering those elements with a plastic contact ball 30 having a substantially semispherical shape. The mount 24 may be composed of a circuit board, for example. The probe 20 is fixed to the probe base 12 by adhesion at the bottom surface of the mount 24.

Each light emitting element 26 functions to apply light to a body tissue 16, and may be composed by an LED. The light receiving element 28 is an element which functions to detect reflected light from the body tissue 16 (for example, the light may be reflected from a hard lump portion 18 within the body tissue 16), and may be composed by a photosensor.

Figure 6:
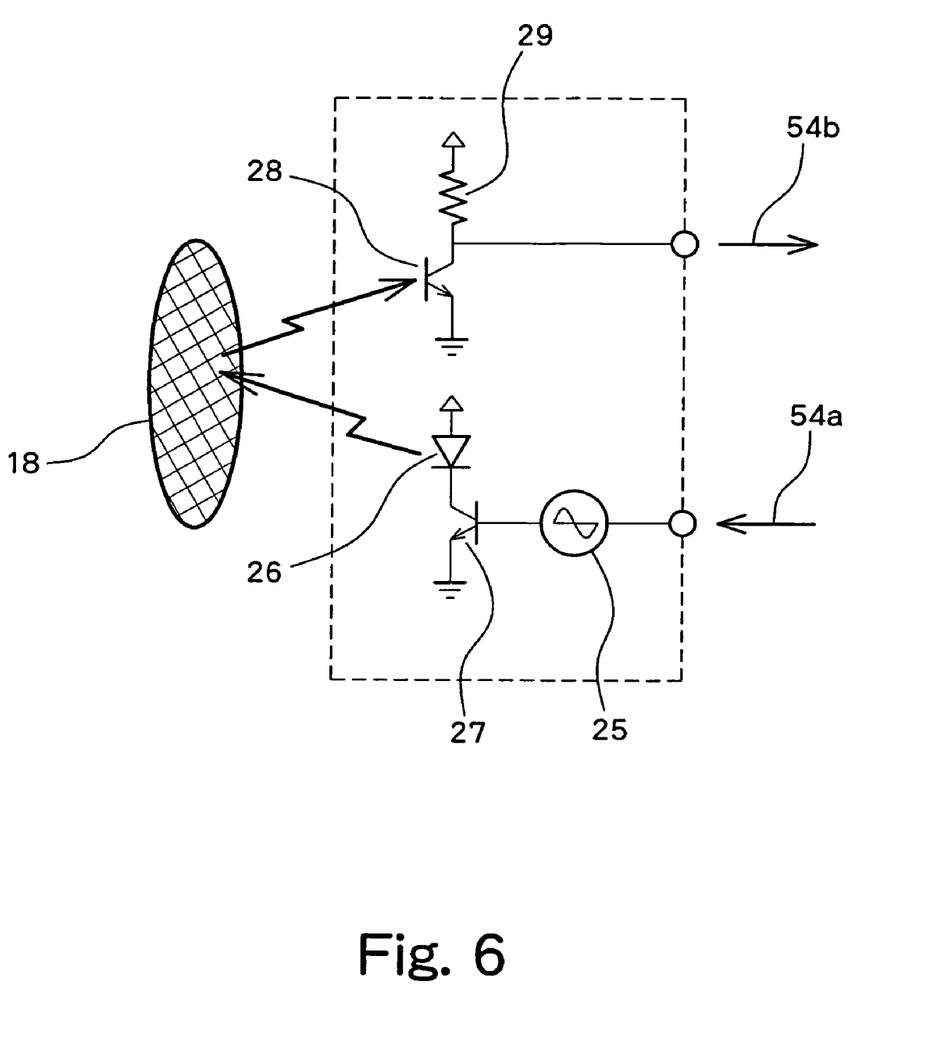
FIG. 6 is a diagram showing a circuit configuration around a light emitting element and a light receiving element in the first embodiment of the present invention.

FIG. 6 is a diagram showing a circuit configuration around a light emitting element 26 and a light receiving element 28. The light emitting element 26 has one terminal connected to a power source and the other terminal connected to a switching element 27. The switching element 27 may be, for example, an npn transistor, and, in such a case, the collector is connected to the other terminal of the light emitting element 26, the emitter is connected to ground, and the base is connected to a signal line 54*a* via an alternating current signal generator 25. The light receiving element 28 has one terminal connected to a power source via a resistor element 29 and the other terminal connected to ground. The connecting portion between the first terminal of the light receiving element 28 and the resistor element 29 is connected to a signal line 54*b*. The signal lines 54*a*, 54*b* are connected to a switch circuit 60 described later. According to the above-described configuration, the switching element 27 is operated in response to an input signal supplied from the signal line 54*a*, and, in accordance with this operation, the light emitting element 26 applies a periodic optical output to a living body. Light reflected from the living body is received by the light receiving element 28. The received light is converted into a voltage signal by the resistor element 29 so as to be output as an output signal to the signal line 54*b*.

The respective electronic components configured as shown in FIG. 6 are wired and arranged on the mount 24, and the contact ball 30 is placed over those components. The contact ball 30 functions to condense incident light and reflected light by means of its semispherical shape. Further, as can be seen in FIG. 5, because of its semispherical shape, the contact ball 30 serves as a member for smoothly contacting the body tissue 16 under pressure when the material property detection apparatus itself is pressed against the body tissue in order to determine the material property of the lump portion 18 or the like located within the body tissue 16. The contact ball 30 may be formed by, for example, supplying plastic resin such as nylon resin on the mount 24 and molding the supplied resin using a semispherical mold. The radius of the semispherical shape may be approximately 5 mm, for example.

Figure 7:
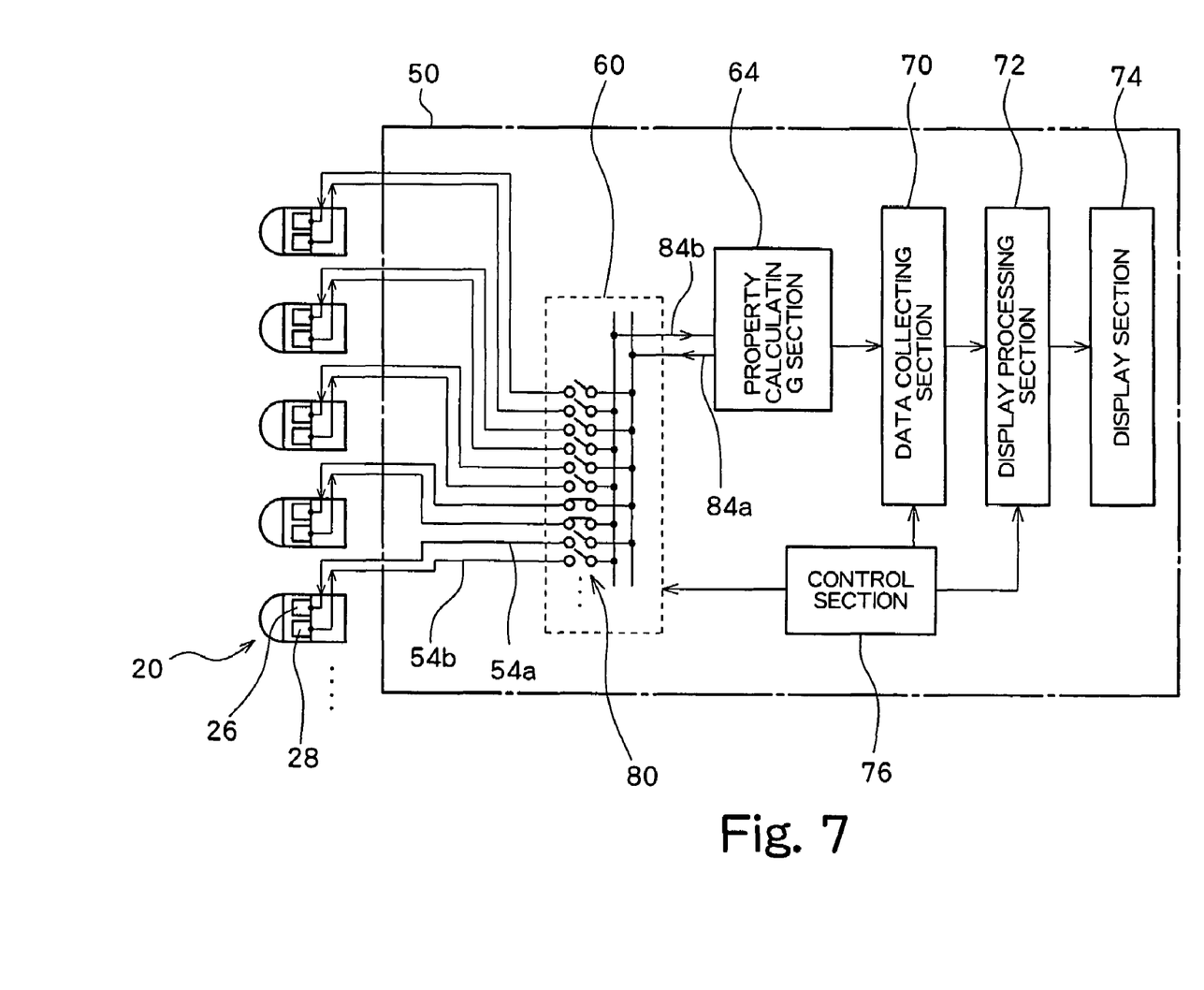
FIG. 7 is a block diagram showing an electronic circuit section in the first embodiment of the present invention.

FIG. 7 is a block diagram showing the electronic circuit section 50. The electronic circuit section 50 includes the switch circuit 60, property calculating section 64, data collecting section 70, display processing section 72, and display section 74, as well as a control section 76 which performs overall control over these components of the electronic circuit section 50.

The switch circuit 60 is a selecting switch circuit which functions to, under control of the control section 76, turn on a particular switch from among a plurality of switches so as to select a particular probe from among the plurality of probes, and connect the selected probe to the property calculating section 64. More specifically, the switch circuit 60 connects the signal line 54*a* to the light emitting element 26 of the selected particular probe to signal line 84*a*, while also connecting the signal line 54*b* from the light receiving element 28 of the selected probe to signal line 84*b*, so as to connect the selected probe via the signal lines 84*a*, 84*b* to the property calculating section 64. The plurality of switches 80 may be implemented using semiconductor switches. The switching of connection may be performed to successively switch to each probe 20. This may be accomplished by, for example, designating an address to each probe 20, and simultaneously connecting the corresponding light emitting element 26 and light receiving element 28 to the property calculating section 64 by applying a scanning method according to the order assigned to the addresses. The scan method may be controlled by the control section 76 and the scanning may be, for example, a line scan in which the arrangement of the probes is regarded as a matrix and the scan is performed row by row. Alternatively, the arrangement of the probes may be regarded as polar coordinates, and the scan may be performed in a spiral manner starting from the center.

The property calculating section 64 is a circuit which performs a calculation regarding each probe 20 selected by the switch circuit 60, based on the signal at the signal input terminal of the light emitting element 26 (i.e., the signal of the signal line 54*a*) and the signal at the signal output terminal of the light receiving element 28 (i.e., the signal of the signal line 54*b*), so as to obtain a material property at the portion of the body tissue opposed by the probe 20. The calculated material property data are sent to the data collecting section 70 while correlating the data to each corresponding probe 20. The above-noted probe addresses may be employed to achieve this correlation.

Figure 8:
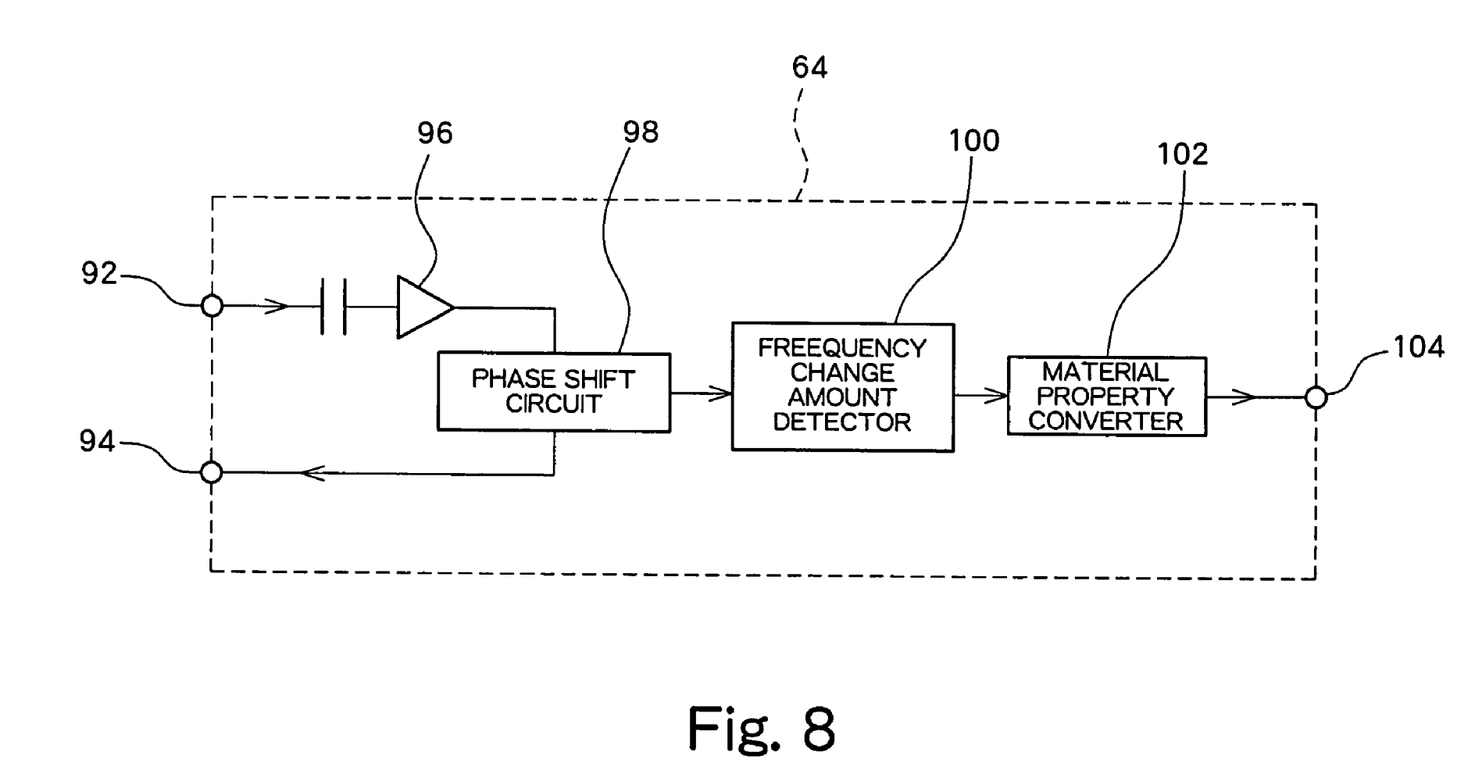
FIG. 8 is a block diagram showing a property calculating section in the first embodiment of the present invention.

FIG. 8 is a block diagram showing the property calculating section 64. The property calculating section 64 includes a terminal 94 connected to the light emitting element 26 in the probe 20 via the signal line (54a) 84a, and a terminal 92 connected to the light receiving element 28 via the signal line (54b) 84b. The property calculating section 64 further includes an amplifier 96 having an input terminal connected to the terminal 92, and a phase shift circuit 98 provided between an output terminal of the amplifier 96 and the terminal 94. The phase shift circuit 98 functions to change a frequency, when a phase difference is generated between the input waveform into the light emitting element 26 and the output waveform from the light receiving element 28, so as to cause this phase difference to become zero. Details of a phase shift circuit having this function are described in the above-referenced Japanese Patent Laid-Open Publication No. Hei 9-145691.

Using the above-described configuration, while maintaining the resonant state of the closed loop including the light emitting element 26, light receiving element 28, and the body tissue, the frequency change generated due to a change in material property in the body tissue is detected by a frequency change amount detector 100, and the detected frequency change is converted into a material property of the body tissue by means of a material property converter 102. A calibration table or the like may be employed in order to convert the frequency change into a material property of the body tissue. When the biological material property to be measured is hardness of the living body, the calibration table can be created by pressing, against the tip of the contact ball, a reference material which can provide a reference hardness, and using a frequency change obtained at that point. As the reference material, it is possible to employ a fat or muscle portion of a normal breast without any hard lumps, or a standard material such as a silicon rubber which is confirmed in advance as having a hardness corresponding to a fat or muscle portion of a normal breast. The converted material property signal is output from the terminal 104.

With regards to oscillation frequency in the resonant state of the closed loop including the light emitting element 26, light receiving element 28, and the body tissue, the center frequency is the frequency of the alternating current signal generator 25 connected to the gate of the light emitting element 26, but this center frequency is changed by the phase shift circuit 98. In other words, the alternating current signal generator 25 is configured such that its frequency can be changed by a feedback provided via the light receiving element 28, amplifier 96, and phase shift circuit 98. For example, the alternating current signal generator 25 may be composed of an LCR circuit and the like. The center frequency of the alternating current signal generator 25 may be within the range from approximately 10 kHz to 1 MHz, as shown in FIG. 1.

The data collecting section 70 is a memory device which stores, for each probe 20, material property data while correlating the data to the respective probes 20. The above-noted probe addresses may be employed to achieve this correlation.

The display processing section 72 is a circuit which reads out necessary data from the data collecting section 70 and performs signal processing for providing a two-dimensional display of the material data. For example, when the display section 74 is composed of a two-dimensional arrangement of multiple display elements 40 as shown in FIG. 2, the display processing section 72 performs processing for correlating outputs for the respective display elements with the two-dimensional arrangement of the probes 20. More specifically, the correlation processing is performed such that, when the display section 74 is observed, each display element 40 indicates the material property detected by a probe 20 located directly under the display element 40, on the opposite side of the probe base 12.

Further, concerning the material property of the overall measured region, an average value, maximum value, minimum value, standard deviation, and the like may be calculated, or a statistical processing such as forming a histogram of the material property distribution may be performed, and subsequently, a display processing for providing a display using text data or the like may be performed.

The data obtained as a result of the display processing is output to the display section 74. The display section 74 is formed by two-dimensionally arranging a plurality of display elements 40, preferably in an arrangement corresponding to the two-dimensional arrangement of the plurality of probes. The plurality of display elements 40 may be, for example, light emitting elements such as light emitting diodes, or two-dimensionally arranged pixels of a liquid crystal display.

It is possible to use brightness of the display elements to denote the biological material property, which may be hardness. For example, hardness may be expressed by increasing the brightness as the hardness value of the body tissue increases, that is, as the degree of seriousness of a hard lump increases. Alternatively, it is possible to employ variable color LEDs or a color liquid crystal display to indicate hardness by means of color differences or color gradation. For example, the degree of a hard lump can be visually expressed by changing the displayed color from blue to yellow to red as the hardness value of the biological tissue increases from a small value to a large value.

When the data collecting section 70 is employed as a temporary storage device used for calculation processing by the display processing section 70, material property data corresponding to each probe can be immediately processed and displayed on the display section 74 in real time. Further, when the data collecting section 70 is employed as a storage device for storing past data as a database, data readout from the database can be displayed on the display section 74.

In addition to the display elements 40 arranged in correlation with the respective probes 20, a general small-size display device 42 as shown in FIG. 2 may also be provide. Using this small-size display device 42, it is possible to display data such as statistically processed data including an average value or the like concerning the material property of the overall measured region, for example.

Figure 9:
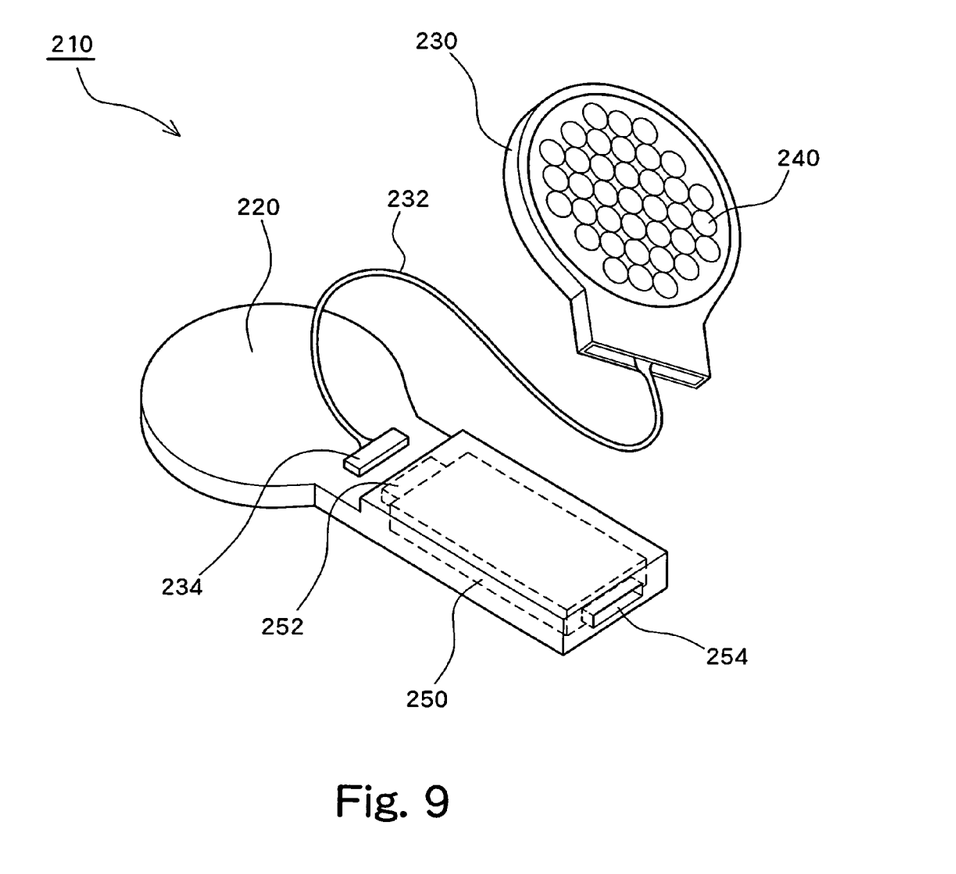
FIG. 9 is a diagram showing a configuration of a material property detection apparatus according to a further embodiment of the present invention.

FIG. 9 is a diagram showing a configuration of a material property detection apparatus 210 according to another embodiment of the present invention. In this material property detection apparatus 210, a main body portion 220 and a display unit portion 230 are formed as separate structures, and those structures are detachably connected via connectors. The display unit portion 230 is a member having a plurality of two-dimensionally arranged display elements 240, and includes a signal line 232. A display-side connector 234 is provided at one end of the signal line 232, and a corresponding base-side connector 252 is provided on the main body portion 220. The base-side connector 252 is connected to the electronic circuit section 250. Further, an external interface 254 is provided on the electronic circuit section 250 in parallel to the base-side connector 252. The display-side connector 234 has a structure which is connectable to both the base-side connector 252 and the external interface 254.

The main body portion 220 and the display unit portion 230 can be fitted on one another at mating portions (not shown) so as to be unified into one unit. More specifically, by connecting the display-side connector 234 with the base-side connector 252, folding and placing the signal line 232 inside a space at the connecting portion of the main body portion 220 or the display unit portion 230, and fitting the main body portion 220 and the display unit portion 230 on one another at the mating portions, the unified material property detection apparatus 210 can be obtained. The external view of the unified material property detection apparatus 210 is identical to that of the material property detection apparatus 10 described in FIG. 2, with the method of use in the unified state being also identical.

Figure 10:
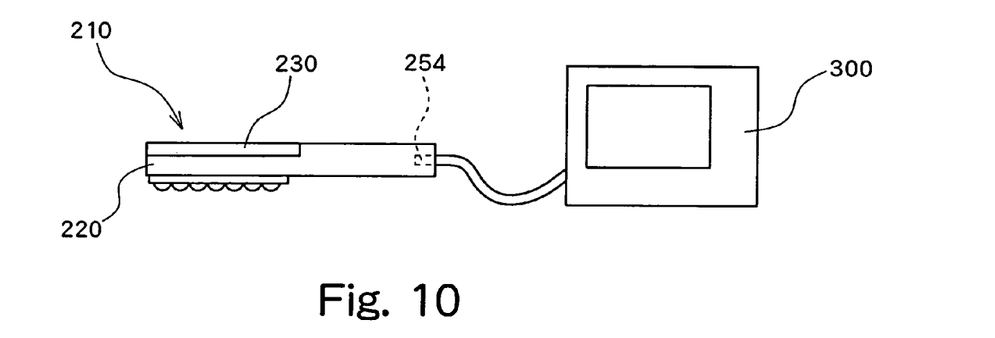
FIG. 10 is a diagram explaining a first method of use according to the further embodiment of the present invention.
Figure 11:
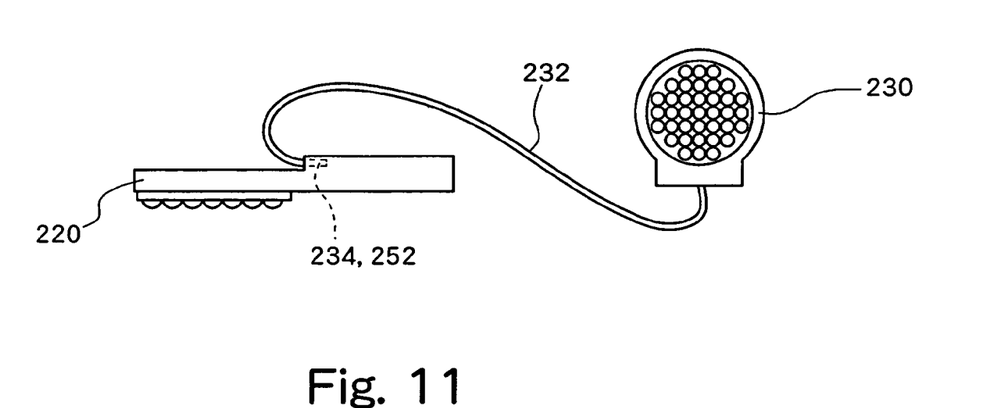
FIG. 11 is a diagram explaining a second method of use according to the further embodiment of the present invention.
Figure 12:
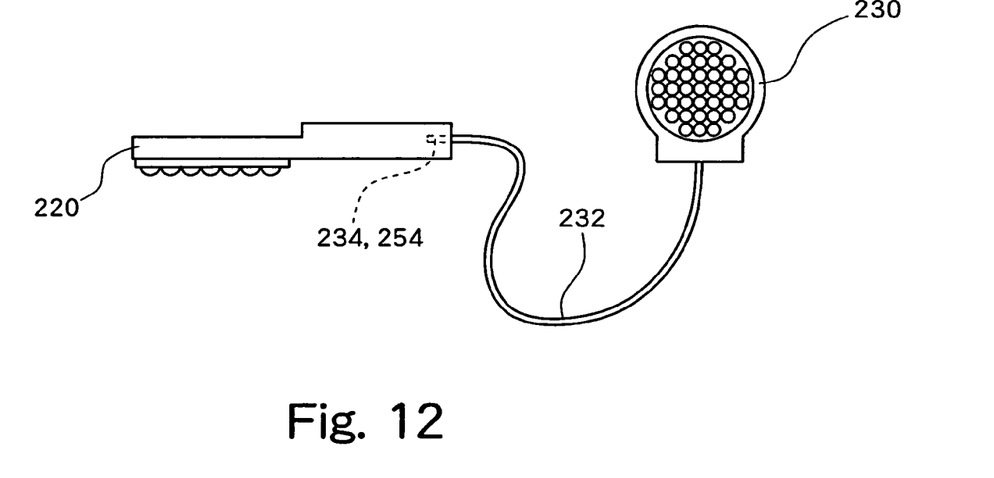
FIG. 12 is a diagram explaining a third method of use according to the further embodiment of the present invention.

According to this material property detection apparatus 210, the degree of freedom in providing display of material property is greatly enhanced. FIGS. 10-12 show examples of material property display methods for the material property detection apparatus 210.

FIG. 10 is a diagram showing an example of a first method of use, which is a method that can be also performed with the material property detection apparatus 10 described in FIG. 2. More specifically, the main body portion 220 and the display unit portion 230 are used in the unified state, and connected to an external diagnostic device 300 using the external interface 254. The external diagnostic device 300 may be, for example, a computer having a larger display screen and higher performance data processing capabilities. According to this method, for example, when the operator performs examination by holding the material property detection apparatus 210 by hand and pressing the material property detection apparatus 210 against a body surface of a person being examined, the operator can observe the condition of a hard lump or the like under the body surface by means of the display unit portion 230, and, at the same time, the individual being examined is able to view the screen of the external diagnostic device 300 and thereby gain an understanding of the examined condition.

FIG. 11 is a diagram showing an example of a second method of use. In this example, the material property detection apparatus is used by detaching the mating between the main body portion 220 and the display unit portion 230 and extending the signal line 232, while maintaining the connection between the display-side connector 234 and the base-side connector 252. According to this method, for example, when an individual performs self-examination by holding the material property detection apparatus 210 by hand and pressing the material property detection apparatus 210 against their own body, they are able to recognize the condition of a hard lump or the like under the body surface by viewing the screen of the display unit portion 230.

FIG. 12 is a diagram showing an example of a third method of use. In this example, the display unit portion 230 is detached from the main body portion 220, while the connection between the display-side connector 234 and the base-side connector 252 is also detached. Further, the display-side connector 234 is connected to the external interface 254. While this method enables the same manner of use as that described in FIG. 11, this method further facilitates operation performed by holding the main body portion 220 by hand because the signal line 232 is connected to an end portion of the main body portion 220.

INDUSTRIAL APPLICABILITY

The detection apparatus for optically determining a biological material property according to the present invention can be employed as a detection apparatus or a diagnostic apparatus for examining a body surface state (such as a tumor) and an internal state (such as a hard lump) in a living body. In particular, it is possible to apply the present invention in an apparatus capable of measuring a biological material property while the probe portion is being held by hand.

The invention claimed is:

1. A detection apparatus for optically determining a biological material property, comprising:
   a probe base;
   a probe supported on the probe base and including a light emitting element for applying light to a living body and a light receiving element for receiving light from the living body;
   an amplifier having an input terminal connected to a signal output terminal of the light receiving element;
   a phase compensation circuit provided between an output terminal of the amplifier and a signal input terminal of the light emitting element for changing a signal frequency so as to cause any phase difference between an input waveform into the light emitting element and an output waveform from the light receiving element to become zero;
   a frequency difference detector which measures a frequency of a self-induced oscillation generated when the phase difference is made to become zero by means of a feedback loop formed by the probe, the amplifier, and the phase compensation circuit, and detects a difference between a frequency obtained when receiving light from the living body by applying light from the probe to the living body and a frequency obtained when such light is not applied to the living body; and
   an output unit for outputting the detected frequency difference as a material property of the living body.

2. A detection apparatus for optically determining a biological material property, comprising:
   a probe base;
   a plurality of probes two-dimensionally arranged and supported on the probe base, each probe including a light emitting element for applying light to a living body and a light receiving element for receiving light from the living body;
   a material property calculator provided so as to be connectable between a signal input terminal of the light receiving element and a signal output terminal of the light emitting element in each probe, for calculating a material property of the living body;
   a switch circuit for successively switching connection of the material property calculator to the respective probes; and
   a display unit for providing a two-dimensional display of the material properties calculated for the respective probes;
   wherein
   the material property calculator comprises:
   an amplifier having an input terminal connected to a signal output terminal of the light receiving element;
   a phase compensation circuit provided between an output terminal of the amplifier and a signal input terminal of the light emitting element for changing the signal frequency so as to cause any phase difference between an input waveform into the light emitting element and an output waveform from the light receiving element to become zero; and
   a frequency difference detector which measures a frequency of a self-induced oscillation generated when the phase difference is made to become zero by means of a feedback loop formed by the probe, the amplifier, and the phase compensation circuit, and detects a difference between a frequency obtained when receiving light from the living body by applying light from the probe to the living body and a frequency obtained when such light is not applied to the living body; and the detection apparatus determines material property of the living body based on a two-dimensional distribution of the frequency differences.

3. A detection apparatus for optically determining a biological material property as defined in claim 2, wherein the display unit is provided on the probe base on a rear surface, located opposite from the surface on which the probes are arranged.

4. A detection apparatus for optically determining a biological material property as defined in claim 3, further comprising:

a receiving portion provided on the rear surface side of the probe base for receiving the display unit;

a base-side connector provided at a portion of the receiving portion for connecting with the display unit; and a signal line drawn out from the display unit and including at one end a display-side connector which is detachably connected to the base-side connector; wherein the display unit is mounted on the receiving portion of the probe base while the display-side connector of the signal line remains connected to the base-side connector.

5. A detection apparatus for optically determining a biological material property as defined in claim 4, wherein the probe base includes an external connector for connecting with an external device; and the display-side connector has a structure which is also connectable to the external connector.

* * * * *